United States Patent
Takayama et al.

(10) Patent No.: US 10,197,654 B2
(45) Date of Patent: Feb. 5, 2019

(54) PET-MRI DEVICE

(71) Applicant: Toshiba Medical Systems Corporation, Otawara-shi (JP)

(72) Inventors: Takuzo Takayama, Utsunomiya (JP); Hitoshi Yamagata, Otawara (JP); Kazuya Okamoto, Saitama (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1219 days.

(21) Appl. No.: 14/452,580

(22) Filed: Aug. 6, 2014

(65) Prior Publication Data

US 2014/0350383 A1    Nov. 27, 2014

Related U.S. Application Data

(63) Continuation of application No. PCT/JP2013/062136, filed on Apr. 24, 2013.

(30) Foreign Application Priority Data

Apr. 24, 2012  (JP) ................................ 2012-099019
Apr. 24, 2013  (JP) ................................ 2013-091777

(51) Int. Cl.
  *G01R 33/48*  (2006.01)
  *A61B 6/00*   (2006.01)
  (Continued)

(52) U.S. Cl.
  CPC .......... *G01R 33/481* (2013.01); *A61B 5/0035* (2013.01); *A61B 5/055* (2013.01);
  (Continued)

(58) Field of Classification Search
  CPC ............ G01R 33/481; G01R 33/56563; G01T 1/1603; A61B 6/583; A61B 6/4417;
  (Continued)

(56) References Cited

U.S. PATENT DOCUMENTS 5,005,578 A * 4/1991 Greer .................. G01R 33/565
                                                         324/318
5,178,146 A * 1/1993 Giese ..................... G01R 33/58
                                                         324/308

(Continued)

FOREIGN PATENT DOCUMENTS

JP  59-157547 A  9/1984
JP  02-152441 A  6/1990

(Continued)

OTHER PUBLICATIONS

Frohwein et al. "Correction of MRI-induced geometric distortions in whole-body small animal PET-MRI." Med Phys: 42(7): pp. 3848-3858 (2015).*

(Continued)

*Primary Examiner* — Amanda Lauritzen Moher
(74) *Attorney, Agent, or Firm* — Oblon, McClelland, Maier & Neustadt, L.L.P.

(57) ABSTRACT

A PET-MRI device according to an embodiment includes image generators and a derivation unit. The image generators capture an image of a target placed in an effective visual field of a PET by the PET and an MRI so as to generate a PET image and an MR image. The derivation unit calculates a strain correction factor for correcting strain on the MR image based on a positional relation between a target that is expressed on the PET image and a target that is expressed on the MR image.

13 Claims, 10 Drawing Sheets

(51) Int. Cl.
   *A61B 5/055* (2006.01)
   *A61B 6/03* (2006.01)
   *A61B 5/00* (2006.01)
   *G01T 1/16* (2006.01)
   *G01R 33/565* (2006.01)
   *G06T 7/00* (2017.01)
   *A61B 6/04* (2006.01)

(52) U.S. Cl.
   CPC ............ *A61B 6/037* (2013.01); *A61B 6/4258* (2013.01); *A61B 6/44* (2013.01); *A61B 6/4417* (2013.01); *A61B 6/5247* (2013.01); *A61B 6/583* (2013.01); *G01R 33/56563* (2013.01); *G01T 1/1603* (2013.01); *A61B 6/0457* (2013.01); *A61B 6/50* (2013.01); *A61B 2576/00* (2013.01); *G06T 7/0012* (2013.01)

(58) Field of Classification Search
   CPC ..... A61B 6/4258; A61B 6/5247; A61B 6/037; A61B 5/0035; A61B 5/055; A61B 6/0457; A61B 2576/00
   See application file for complete search history.

(56) References Cited

U.S. PATENT DOCUMENTS

| | | | | |
|---|---|---|---|---|
| 7,352,840 | B1* | 4/2008 | Nagarkar | A61B 6/032 250/363.02 |
| 2007/0055127 | A1* | 3/2007 | Ladebeck | G01R 33/481 600/407 |
| 2007/0102641 | A1 | 5/2007 | Schmand et al. | |
| 2008/0146914 | A1 | 6/2008 | Polzin et al. | |
| 2008/0269594 | A1* | 10/2008 | Paul | G01R 33/481 600/411 |
| 2009/0072155 | A1* | 3/2009 | Watson | G01T 1/2985 250/363.03 |
| 2009/0108206 | A1* | 4/2009 | Breuer | G01R 33/28 250/363.03 |
| 2009/0146066 | A1* | 6/2009 | Renz | A61B 6/037 250/363.04 |
| 2009/0209844 | A1 | 8/2009 | Gagnon et al. | |
| 2010/0102813 | A1* | 4/2010 | Schulz | A61B 6/037 324/309 |
| 2010/0108896 | A1* | 5/2010 | Surti | G01T 1/00 250/363.04 |
| 2010/0217112 | A1* | 8/2010 | Choi | G01R 33/481 600/411 |
| 2011/0043206 | A1 | 2/2011 | Kimura et al. | |
| 2011/0150312 | A1 | 6/2011 | Takanami et al. | |
| 2011/0224534 | A1 | 9/2011 | Yamaya et al. | |
| 2012/0056621 | A1 | 3/2012 | Blumhagen et al. | |
| 2013/0006091 | A1* | 1/2013 | Manjeshwar | A61B 6/037 600/411 |
| 2013/0234710 | A1 | 9/2013 | Kanno et al. | |
| 2013/0241555 | A1 | 9/2013 | Obata et al. | |
| 2013/0296689 | A1 | 11/2013 | Okamoto et al. | |
| 2013/0324836 | A1 | 12/2013 | Yamaya et al. | |

FOREIGN PATENT DOCUMENTS

| | | |
|---|---|---|
| JP | 2006-116216 A | 5/2006 |
| JP | 2006-141782 A | 6/2006 |
| JP | 2008-525161 A | 7/2008 |
| JP | 2010-017421 A | 1/2010 |
| JP | 2010-508079 A | 3/2010 |
| JP | 2011-062508 A | 3/2011 |
| WO | WO 2007/125676 A1 | 11/2007 |
| WO | WO 2012/060304 A1 | 5/2012 |

OTHER PUBLICATIONS

Delvin et al. "Susceptibility-Induced Loss of Signal: Comparing PET and fMRI on a Semantic Task." NeuroImage: 11(6): pp. 589-600 (2000).*

International Search Report dated Jun. 4, 2013 for PCT/JP2013/062136 Filed on Apr. 24, 2013 (English Translation).

International Written Opinion dated Jun. 4, 2013 for PCT/JP2013/062136 Filed on Apr. 24, 2013.

U.S. Appl. No. 14/522,024, filed Oct. 23, 2014, Okamoto, et al.

U.S. Appl. No. 13/873,706, filed Apr. 30, 2013, 2013-0234710, Kanno, et al.

U.S. Appl. No. 13/874,795, filed May 1, 2013, 2013-0241555, Obata, et al.

U.S. Appl. No. 13/938,592, filed Jul. 10, 2013, 2013-0324836, Yamaya, et al.

U.S. Appl. No. 13/935,812, filed Jul. 5, 2013, 2013-0296689, Okamoto, et al.

* cited by examiner

PET-MRI DEVICE

CROSS-REFERENCE TO RELATED APPLICATIONS

This application is a continuation of PCT international application Ser. No. PCT/JP2013/062136 filed on Apr. 24, 2013 which designates the United States, incorporated herein by reference, and which claims the benefit of priority from Japanese Patent Application No. 2012-099019 filed on Apr. 24, 2012; and Japanese Patent Application No. 2013-091777, filed on Apr. 24, 2013, the entire contents of which are incorporated herein by reference.

FIELD

Embodiments described herein relate generally to a PET-MRI device.

BACKGROUND

In recent years, expected has been wider use of a "PET-MRI device" that is a combination of a positron emission tomography device (PET device) and a magnetic resonance imaging device (MRI device). For example, the PET-MRI device is expected to be used for early diagnosis of Alzheimer's disease. Conventionally, in image capturing by the MRI device, known has been a fact that strain is generated on an MR image due to non-uniformity of a magnetostatic field.

DETAILED DESCRIPTION

A PET-MRI device according to an embodiment includes image generators and a derivation unit. The image generators capture an image of a target placed in an effective visual field of a PET by the PET and an MRI so as to generate a PET image and an MR image. The derivation unit calculates a strain correction factor for correcting strain on the MR image based on a positional relation between a target that is expressed on the PET image and a target that is expressed on the MR image.

Hereinafter, a PET-MRI device according to an embodiment is described in detail with reference to the accompanying drawings.

Figure 1:
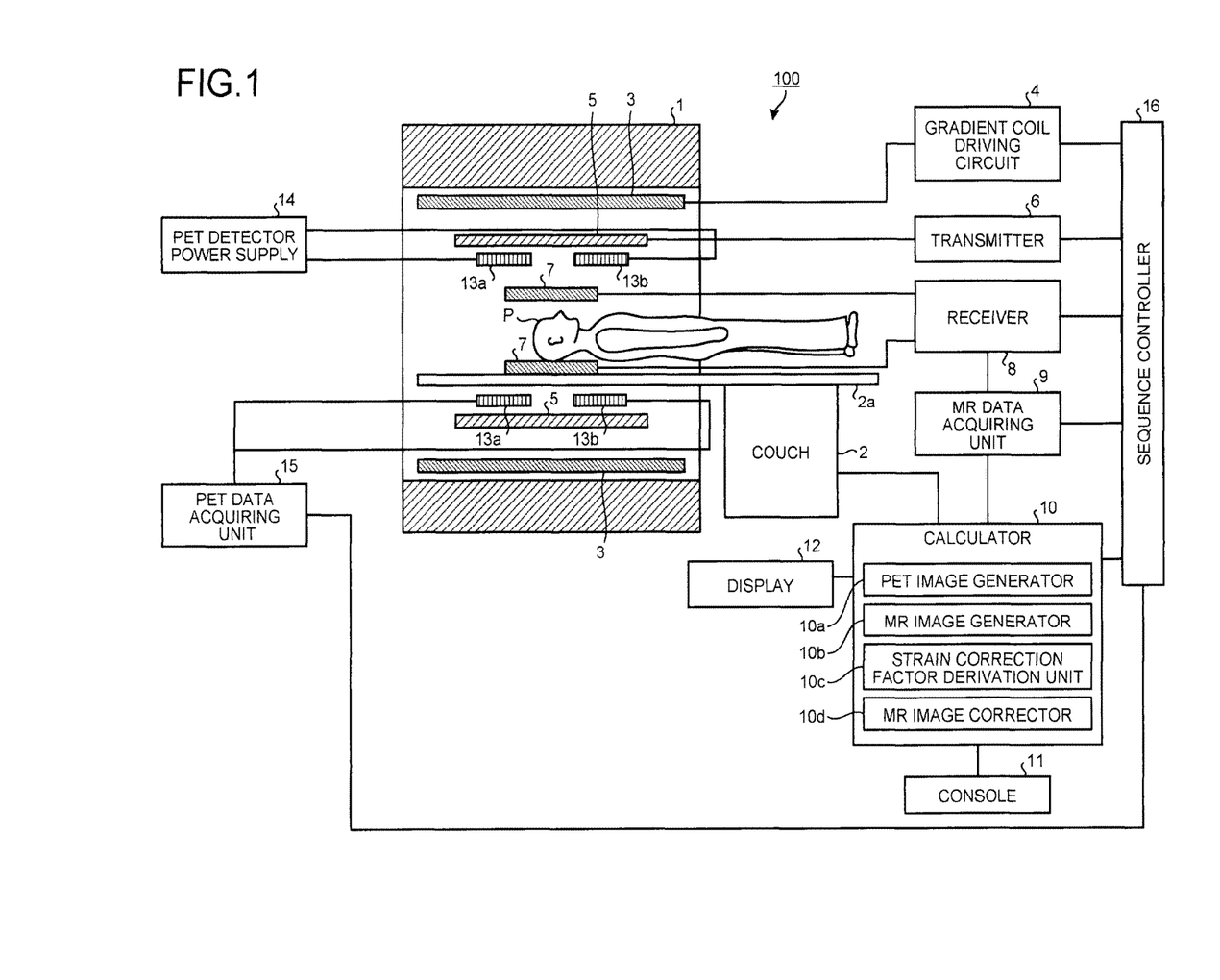
FIG. 1 is a view illustrating a configuration of a PET-MRI device according to an embodiment.

FIG. 1 is a view illustrating a configuration of a PET-MRI device 100 according to the embodiment. As illustrated in FIG. 1, the PET-MRI device 100 includes a magnetostatic field magnet 1, a couch 2, a gradient coil 3, a gradient coil driving circuit 4, a transmission high-frequency coil 5, a transmitter 6, receiving high-frequency coils 7, a receiver 8, a magnetic resonance (MR) data acquiring unit 9, a calculator 10, a console 11, a display 12, PET detectors 13a and 13b, a PET detector power supply 14, a PET data acquiring unit 15, and a sequence controller 16.

The magnetostatic field magnet 1 generates a magnetostatic field in a space in a bore. The bore is a substantially cylindrical structure accommodating the magnetostatic field magnet 1, the gradient coil 3, and the like. The couch 2 includes a couchtop 2a on which a subject P is placed. The couchtop 2a of the couch 2 is moved into the bore so as to move the subject P into the magnetostatic field.

The gradient coil 3 applies gradient magnetic fields Gx, Gy, and Gz. In the gradient magnetic fields Gx, Gy, and Gz, magnetic field strengths in the same direction as the magnetostatic field change substantially linearly with respect to distances from the center of the magnetic field in the X, Y, and Z directions. The gradient coil 3 is formed into a substantially cylindrical form and is arranged at the inner circumferential side of the magnetostatic field magnet 1. The gradient coil driving circuit 4 drives the gradient coil 3 under the control of the sequence controller 16.

The transmission high-frequency coil 5 applies a high-frequency magnetic field to the subject P placed in the magnetostatic field based on a high-frequency pulse transmitted from the transmitter 6. The transmission high-frequency coil 5 is formed into a substantially cylindrical form and is arranged at the inner circumferential side of the gradient coil 3. The transmitter 6 transmits the high-frequency pulse to the transmission high-frequency coil 5 under the control of the sequence controller 16.

The receiving high-frequency coils 7 detect a magnetic resonance signal emitted from the subject P by application of the high-frequency magnetic field and the gradient magnetic field. For example, the receiving high-frequency coils 7 are surface coils arranged on the surfaces of the subject P in accordance with a site to be image-captured. The receiver 8 receives the magnetic resonance signal detected by the receiving high-frequency coils 7 under the control of the sequence controller 16. Furthermore, the receiver 8 transmits the received magnetic resonance signal to the MR data acquiring unit 9.

The MR data acquiring unit 9 acquires the magnetic resonance signal transmitted from the receiver 8 under the control of the sequence controller 16. Furthermore, the MR data acquiring unit 9 amplifies and detects the acquired magnetic resonance signal, and then, analog (A)-to-digital (D)-converts it so as to generate MR data. Then, the MR data acquiring unit 9 transmits the generated MR data to the calculator 10.

The PET detectors 13a and 13b detect annihilation radiation (hereinafter, "gamma rays") emitted from a positron-emitting radionuclide administered to the subject P as count information. The PET detectors 13a and 13b transmit the detected count information to the PET data acquiring unit 15. The PET detectors 13a and 13b are formed into ring forms and are arranged at the inner circumferential side of the transmission high-frequency coil 5. For example, each of the PET detectors 13a and 13b is formed by arranging detector modules having scintillators and optical detectors in a ring form. The scintillators are formed of lutetium yttrium oxyorthosilicate (LYSO), lutetium oxyorthosilicate (LSO) or lutetium gadolinium oxyorthosilicate (LGSO), for example. The optical detectors are semiconductor detectors such as avalanche photodiode (APD) elements and silicon photomultipliers (SiPM), or photomultiplier tubes (PMT), for example.

The PET detector power supply 14 supplies electric power for driving the optical detectors to the PET detectors 13a and 13b. The PET data acquiring unit 15 acquires pieces of the count information transmitted from the PET detectors 13a and 13b under the control of the sequence controller 16. Furthermore, the PET data acquiring unit 15 generates, as PET data, coincidence information as a combination of the pieces of count information obtained by detecting the gamma rays at substantially the same time by using the pieces of acquired count information. Then, the PET data acquiring unit 15 transmits the generated PET data to the calculator 10.

The sequence controller 16 controls the above-mentioned parts based on various types of image capturing sequences to be executed at the time of image capturing.

Figure 2:
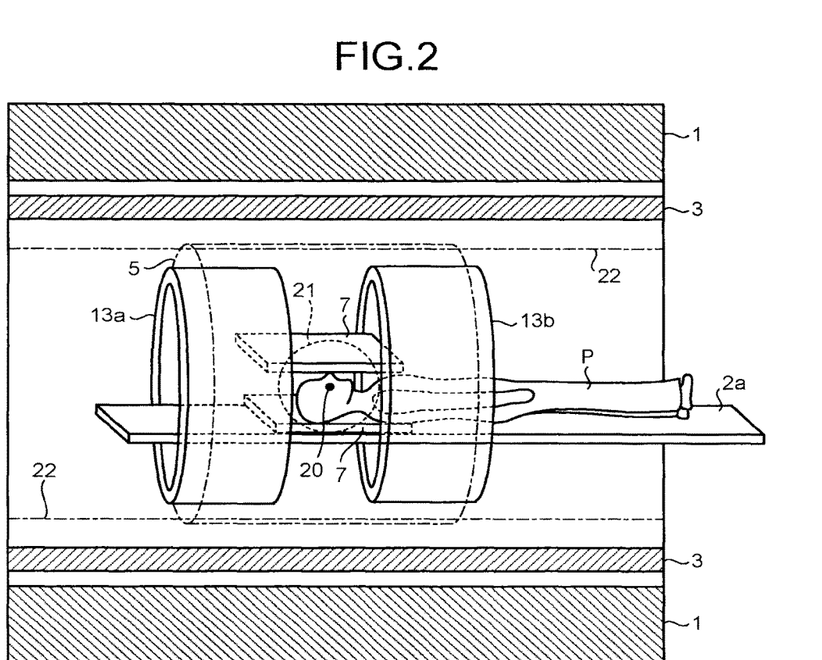
FIG. 2 is a view illustrating the arrangement of parts around PET detectors in the embodiment.
Figure 3:
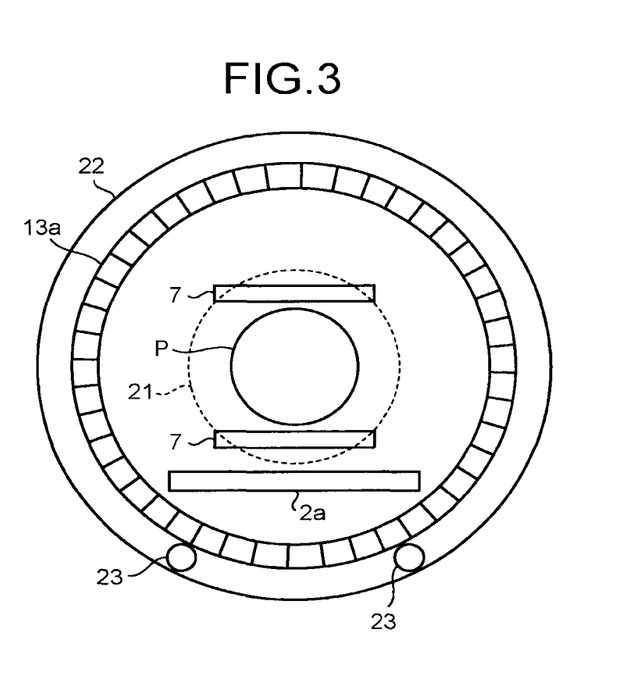
FIG. 3 is a view illustrating the arrangement of parts around the PET detectors in the embodiment.

FIGS. 2 and 3 are views illustrating the arrangement of parts around the PET detectors 13a and 13b in the embodiment. In FIG. 2, a point 20 indicates the magnetic field center of the magnetostatic field. In FIG. 2, a substantially spherical region 21 surrounded by a dotted line indicates an effective visual field of the MRI. In FIG. 2, a dashed-dotted line 22 indicates a bore inner wall.

As illustrated in FIG. 2, the PET detectors 13a and 13b are arranged at the inner circumferential side of the bore in the embodiment. The PET detectors 13a and 13b are arranged with a space therebetween in the shaft direction of the bore so as to sandwich the magnetic field center 20 of the magnetostatic field generated by the magnetostatic field magnet 1. That is to say, in the embodiment, the PET detectors 13a and 13b are arranged so as to stay away from the vicinity of the magnetic field center 20 as the effective visual field of the MRI. This suppresses image deterioration of an MR image due to the PET detectors.

The PET-MRI device 100 includes movement mechanisms for moving the PET detectors 13a and 13b along the shaft direction of the bore. FIG. 3 is a view illustrating the arrangement of parts when the inner portion of the bore is seen from an opening at the side at which the PET detector 13a is arranged. For example, as illustrated in FIG. 3, movement mechanisms 23 are two rails installed on a lower portion of the bore inner wall 22. The movement mechanisms 23 are fitted into rail bearings formed on the outer circumferential surface of the PET detector 13a in groove forms. The movement mechanisms 23 support the PET detector 13a such that the PET detector 13a is movable along the shaft direction of the bore. The movement mechanisms 23 for moving the PET detector 13b are also provided at the side of the PET detector 13b in the same manner.

The PET detectors 13a and 13b can be attached to and detached from the respective movement mechanisms 23 and can be inserted into and removed from both sides of the openings of the bore. This configuration, in which the PET detectors 13a and 13b are attachable and detachable, enables the PET detectors to be incorporated into conventional MRI devices relatively easily, so that the use of the PET-MRI device can be spread widely.

Figure 4:
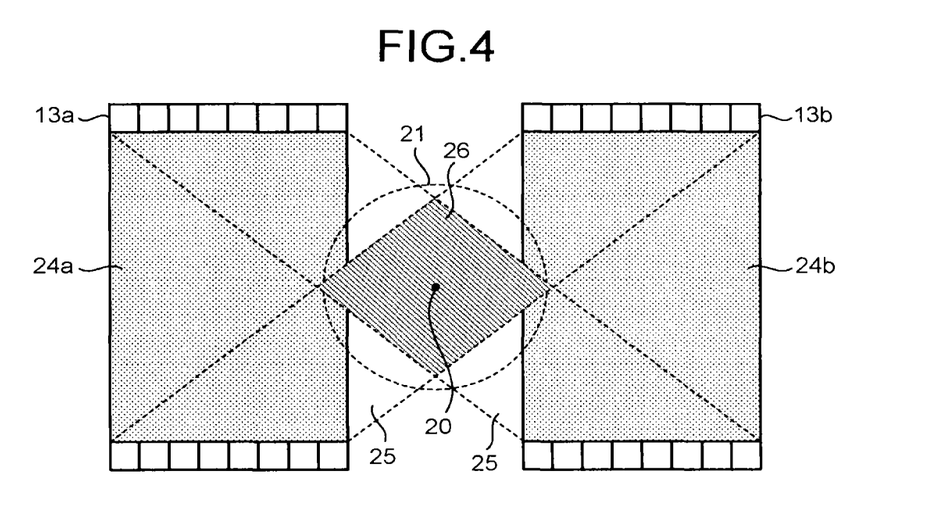
FIG. 4 is a view illustrating effective visual fields of a PET and an MRI in the embodiment.

Next, FIG. 4 is a view illustrating effective visual fields of the PET and the MRI in the embodiment. The effective visual fields are regions in which data (in a range in which image quality is guaranteed) effective as data to be imaged can be acquired. In the PET-MRI device 100, the effective visual fields include a "PET effective visual field" in which data effective for a PET image can be acquired, an "MRI effective visual field" in which data effective for an MR image can be acquired, and a "PET-MRI effective visual field" in which data effective for both the PET image and the MR image can be acquired.

First, as illustrated in FIG. 4, the MRI effective visual field is the substantially spherical region 21 whose center corresponds to the magnetic field center 20 generally. The PET effective visual field includes a region 24a surrounded by the inner circumferential surface of the PET detector 13a, and a region 24b surrounded by the inner circumferential surface of the PET detector 13b. Furthermore, regions 25 formed by the inner circumferential surface of the PET detector 13a and the inner circumferential surface of the PET detector 13b can be also considered as the PET effective visual field.

Based on this, the PET-MRI effective visual field corresponds to an overlapped portion of the PET effective visual field and the MRI effective visual field, that is, an overlapped portion of the MRI effective visual field 21 and the PET effective visual field 24a, 24b, or 25. In FIG. 4, a rhombic region 26 is a region having a shape obtained by bonding the bottom surfaces of circular cones. The region 26 may be considered as the PET-MRI effective visual field in view of guaranteeing image quality. The PET-MRI effective visual field illustrated in FIG. 4 is an example and is not limited thereto. For example, if the PET detectors 13a and 13b are moved, the length of the PET-MRI effective visual field in the direction perpendicular to the shaft direction of the bore can be changed. In addition, the PET-MRI effective visual field can be changed depending on the sizes of the PET detectors 13a and 13b, for example.

Furthermore, the PET-MRI device 100 according to the above-mentioned embodiment corrects strain on the MR image by using the PET image. Strain is generated on the MR image due to non-uniformity of the magnetostatic field in some cases. On the other hand, such strain is not generated on the PET image. The PET-MRI device according to the embodiment captures an image of a target placed in the PET effective visual field by the PET and the MRI so as to derive a strain correction factor for correcting the strain on the MR image by using the PET image with no strain.

This processing is mainly performed by the parts included in the calculator 10. As illustrated in FIG. 1, the calculator 10 includes a PET image generator 10a, an MR image generator 10b, a strain correction factor derivation unit 10c, and an MR image corrector 10d. The calculator 10 receives an operation by an operator through the console 11. Furthermore, the calculator 10 displays the PET image, the MR image, and the like on the display 12.

The PET image generator 10a captures an image of the target placed in the PET effective visual field so as to generate a PET image. For example, the PET image generator 10a controls the sequence controller 16, the PET detectors 13a and 13b, the PET detector power supply 14, the PET data acquiring unit 15, and the like so as to capture an image of the target. Furthermore, the PET image generator 10a reconstructs the PET data generated by the PET data acquiring unit 15 so as to generate the PET image. The MR image generator 10b captures an image of the target that is the same as the target to be image-captured by the PET image generator 10a so as to generate an MR image. For example, the MR image generator 10b controls the sequence controller 16, the gradient coil driving circuit 4, the transmitter 6, the receiver 8, the MR data acquiring unit 9, and the like so as to capture an image of the same target. Furthermore, the MR image generator 10b reconstructs the MR data generated by the MR data acquiring unit 9 so as to generate the MR image.

The strain correction factor derivation unit 10c derives a strain correction factor for correcting the strain on the MR image based on a positional relation between the target that is expressed on the PET image generated by the PET image generator 10a and the target that is expressed on the MR image generated by the MR image generator 10b. Furthermore, the MR image corrector 10d corrects the MR image by using the strain correction factor derived by the strain correction factor derivation unit 10c.

Figure 5:
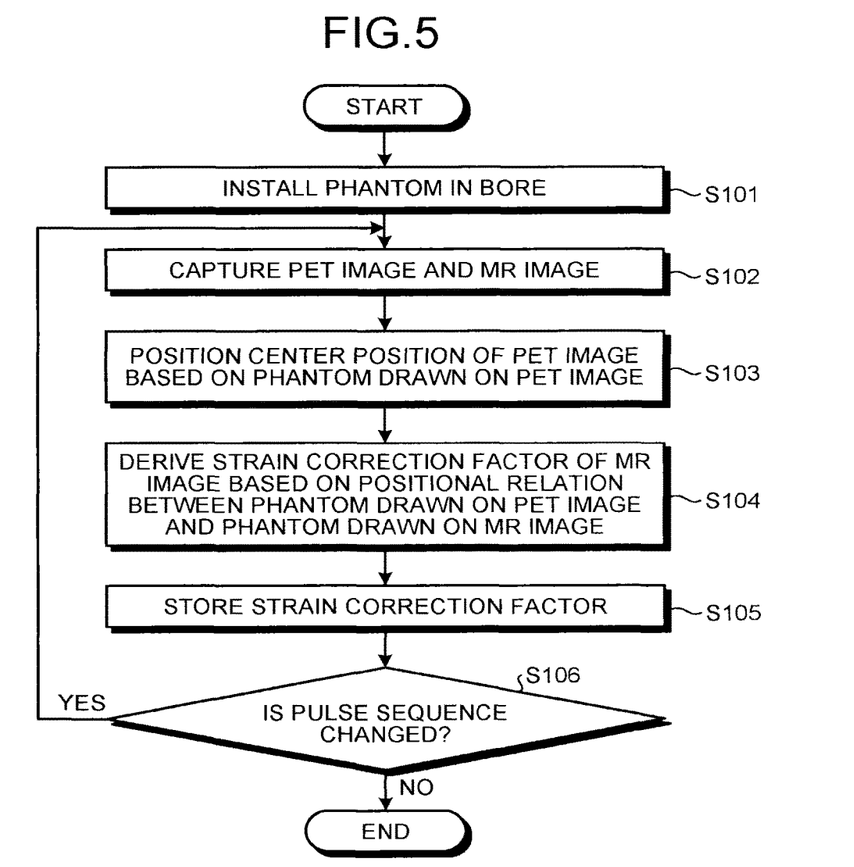
FIG. 5 is a flowchart illustrating strain correction factor derivation processing in the embodiment.
Figure 6A:
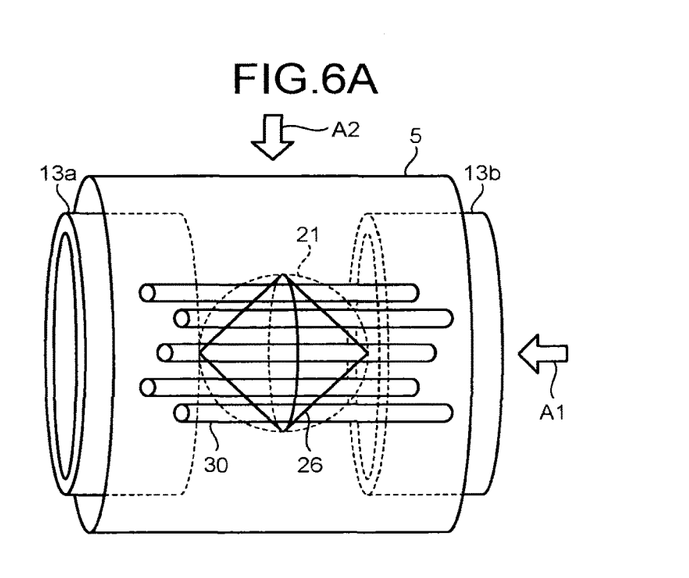
FIG. 6A is a view for explaining phantoms in the embodiment.
Figure 6B:
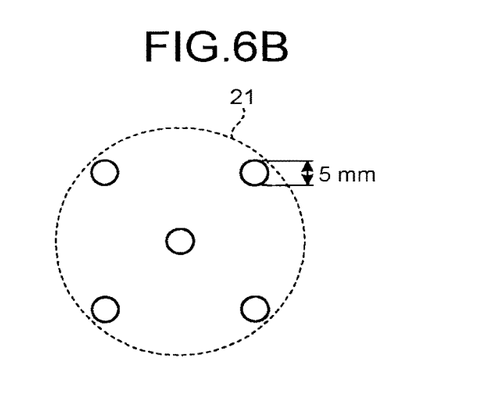
FIG. 6B is a view for explaining the phantoms in the embodiment.
Figure 6C:
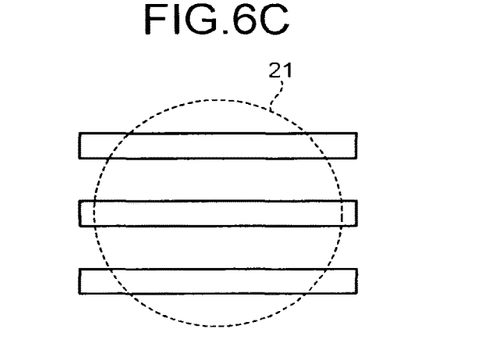
FIG. 6C is a view for explaining the phantoms in the embodiment.

Hereinafter, explanation is made by using a specific example. FIG. 5 is a flowchart illustrating the strain correction factor derivation processing in the embodiment. FIGS. 6A to 6C are views for explaining phantoms 30 in the embodiment. FIG. 6B is a view of the phantoms 30 seen from the direction of an arrow A1 in FIG. 6A. FIG. 6C is a view of the phantoms 30 seen from the direction of an arrow A2 in FIG. 6A.

In the embodiment, it is assumed that the strain correction factor derivation processing illustrated in FIG. 5 is executed when the PET-MRI device 100 is installed. Conventionally, various types of adjustments are executed when PET devices and MRI devices are installed. It is sufficient that the strain correction factor derivation processing illustrated in FIG. 5 is executed as one of the adjustments, for example. The embodiment is not limited thereto. The execution timing of the strain correction factor derivation processing is not limited to the time of the installation and it may be executed while the PET-MRI device 100 is being operated, for example.

The strain correction factor derivation unit 10c in the embodiment derives a strain correction factor for each pulse sequence of the MRI. That is to say, it is considered that the strain on the MR image is generated due to the non-uniformity of the magnetostatic field, and the non-uniformity of the magnetostatic field depends on the type of the pulse sequence. For example, echo planar imaging (EPI) is ultra-fast imaging that acquires all the magnetic resonance signals for reconstructing an image with one excitation pulse and has been known as a pulse sequence that is largely influenced by the non-uniformity of the magnetostatic field. Thus, it is considered that the non-uniformity of the magnetostatic field depends on the type of the pulse sequence. For this reason, the strain correction factor derivation unit 10c in the embodiment executes various types of representative pulse sequences that are influenced by the non-uniformity of the magnetostatic field so as to derive the strain correction factor for each of the pulse sequences of the MRI.

As illustrated in FIG. 5, first, the phantoms 30 are arranged in the bore of the PET-MRI device 100 (step S101). Each of the phantoms 30 in the embodiment has a linear shape extending in the shaft direction of the bore. For example, the phantoms 30 are formed by five tubes extending in the shaft direction of the bore, as illustrated in FIG. 6A. The phantoms 30 incorporate radioisotopes and hydrogen nuclei, whereby imaging by both the PET and the MRI can be executed. For example, the phantoms 30 are formed by tubes injected with water in which fluorodeoxy glucose (FDG) is melted.

As illustrated in FIGS. 6B and 6C, the phantoms 30 are placed in the PET effective visual field and on a side edge portion of the effective visual field of the MRI. That is to say, as described above, the strain correction factor is derived under the assumption that strain is not generated on the PET image. Based on the assumption, it is desired that an image of the phantoms 30 is captured while being placed in the PET image effective visual field. The strain on the MR image is generated more heavily on the side edge portion of the image than in the center portion of the image. This indicates that the phantoms 30 are desirably placed on the side edge portion of the effective visual field 21 of the MRI. Furthermore, because the strain correction factor is derived under the assumption that strain is not generated on the PET image, it is desired that the tubes of the phantoms 30 have the thicknesses (for example, equal to or smaller than 5 mm) within a spatial resolution of the PET.

Subsequently, returning to FIG. 5, the PET image generator 10a and the MR image generator 10b capture an image of the phantoms 30 installed in the bore at step S101 so as to generate the PET image and the MR image, respectively (step S102). For example, the PET image generator 10a and the MR image generator 10b capture an image of the phantoms 30 over a plurality of slices while shifting a slice position of the target to be imaged in the shaft direction of the bore. The image capturing by the PET image generator 10a and the image capturing by the MR image generator 10b may be executed at the same time or may be executed independently in the any desired order.

Next, the strain correction factor derivation unit 10c positions the center position of the PET image based on the phantoms 30 drawn on the PET image (step S103). For example, in the embodiment, five tubes are drawn on the PET image, as illustrated in FIG. 6B. The strain correction factor derivation unit 10c determines whether the center tube among the five tubes drawn on the PET image is positioned at the image center of the PET image. Then, when the strain correction factor derivation unit 10c has determined that the center tube is not positioned at the image center, it shifts the PET image parallel so as to position the center position of the PET image. In addition, the strain correction factor derivation unit 10c positions the center position of the MR image in the same manner. The positioning of the center position may be performed manually by displaying the PET image or the MR image on the display 12 once and receiving an operation by an operator.

Then, the strain correction factor derivation unit 10c derives a strain correction factor based on the positional relation between the phantoms 30 drawn on the PET image and the phantoms 30 drawn on the MR image (step S104).

Figure 7:
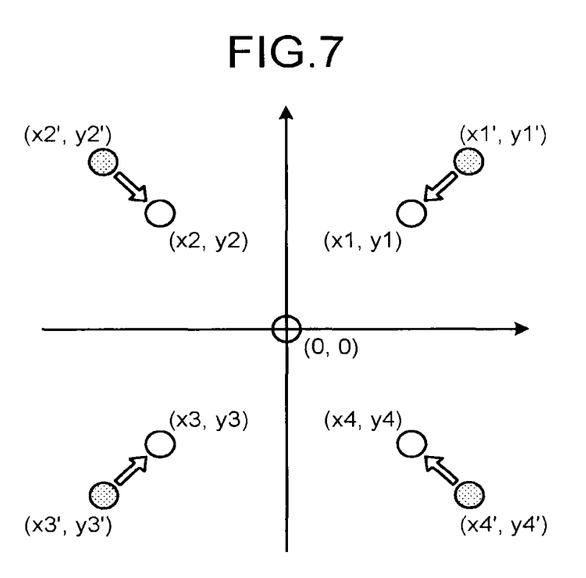
FIG. 7 is a view for explaining a strain correction factor in the embodiment.

FIG. 7 is a view for explaining the strain correction factor in the embodiment. For example, in FIG. 7, white circles indicate the phantoms 30 drawn on the PET image and gray circles indicate the phantoms 30 drawn on the MR image. In the embodiment, positioning of the centers of both the PET image and the MR image is completed. In FIG. 7, an overlapped portion of the center tube drawn on the PET image and the center tube drawn on the MR image is indicated by a white circle.

As described above, because strain is not generated on the PET image, it is considered that deviations between the white circles and the gray circles are generated due to the strain on the MR image. In view of this, the strain correction factor derivation unit 10c obtains a function of coordinate conversion for making the gray circles drawn on the MR image identical to the white circles drawn on the PET image so as to derive the strain correction factor. For example, the strain correction factor derivation unit 10c derives a coordinate conversion matrix for converting coordinates (x1', y1') in the first quadrant to coordinates (x1, y1), converting coordinates (x2', y2') in the second quadrant to coordinates (x2, y2), converting coordinates (x3', y3') in the third quadrant to coordinates (x3, y3), and converting coordinates (x4', y4') in the fourth quadrant to coordinates (x4, y4).

Thereafter, the strain correction factor derivation unit 10c stores the strain correction factor derived at step S104 in a storage unit (not illustrated) in a manner corresponding to identification information of the pulse sequence (step S105). Thereafter, the strain correction factor derivation unit 10c determines whether the pulse sequence is changed (step S106). When the strain correction factor derivation unit 10c has determined that there is an unexecuted pulse sequence (Yes at step S106), the strain correction factor derivation unit 10c changes the pulse sequence and the process is returned to the processing at step S102. When the strain correction factor derivation unit 10c has determined that the strain correction factor derivation processing has been finished for all the pulse sequences (No at step S106), the processing is finished.

The strain correction factor that has been derived and stored in the storage unit in this manner is used after the PET-MRI device 100 has been installed completely and started to be operated. That is to say, if the MRI in the PET-MRI device 100 has captured an image and an MRI image has been acquired, the PET-MRI device 100 corrects the strain on the MR image by using the strain correction factor derived at the time of the installation.

Figure 8:
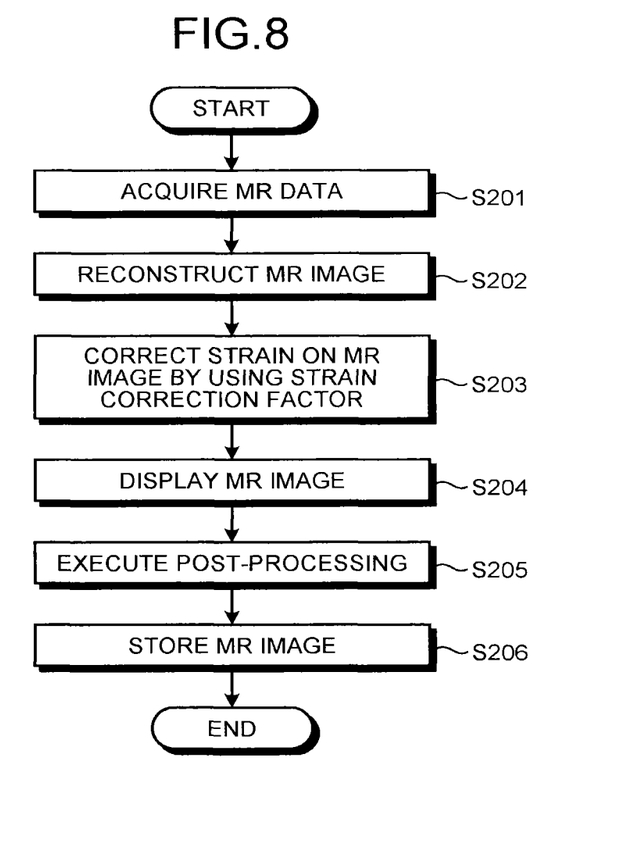
FIG. 8 is a flowchart illustrating strain correction processing in the embodiment.

FIG. 8 is a flowchart illustrating the strain correction processing in the embodiment. As illustrated in FIG. 8, the MR image generator 10b controls the sequence controller 16, the gradient coil driving circuit 4, the transmitter 6, the receiver 8, the MR data acquiring unit 9, and the like so as to capture an image of the subject P and acquire MR data (step S201). Subsequently, the MR image generator 10b reconstructs the MR data generated by the MR data acquiring unit 9 so as to generate an MR image (step S202).

Next, the MR image corrector 10d acquires the strain correction factor that has been made to correspond to the identification information of the pulse sequence used for acquisition of the MR data at step S201 from the storage unit (not illustrated) and corrects the MR image generated at step S202 by using the acquired strain correction factor (step S203).

Thereafter, the calculator 10 displays the MR image corrected at step S203 on the display 12 (step S204), executes post-processing on the MR image corrected at step S203 (step S205), and then, stores the MR image in the storage unit (step S206). The pieces of processing at steps S204 to S206 may be omitted as appropriate or the order thereof may be changed.

Thus, according to the embodiment, strain on the MR image is corrected by using the PET image with no strain, so that the strain on the MR image can be corrected appropriately.

Although the embodiment describes the linear phantoms 30 extending in the shaft direction of the bore as an example, the embodiment is not limited thereto.

Figure 9A:
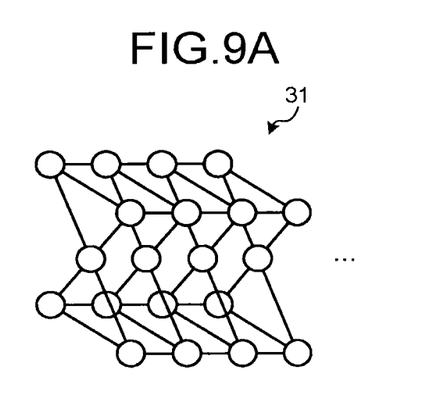
FIG. 9A is a view for explaining phantoms according to a modification of the embodiment.
Figure 9B:
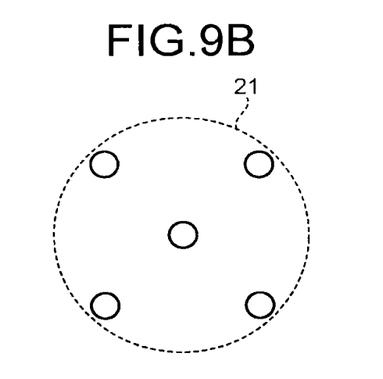
FIG. 9B is a view for explaining the phantoms in the modification of the embodiment.
Figure 9C:
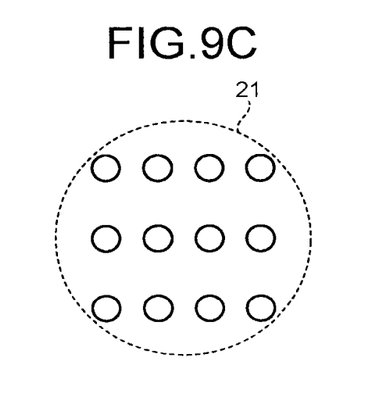
FIG. 9C is a view for explaining the phantoms in the modification of the embodiment.

FIGS. 9A to 9C are views for explaining phantoms 31 according to a modification of the embodiment. FIG. 9B is a view of the phantoms 31 seen from the direction of the arrow A1 in FIG. 6A as in FIG. 6B, and FIG. 9C is a view of the phantoms 31 seen from the direction of the arrow A2 in FIG. 6A as in FIG. 6C. For example, each of the phantoms 31 according to the modification of the embodiment has a dot-like shape scattered in the shaft direction of the bore as illustrated in FIG. 9A. Furthermore, as with the phantoms 30, the phantoms 31 incorporate radioisotopes and hydrogen nuclei so as to execute imaging by both the PET and the MRI. For example, the phantoms 31 are formed by spheres injected with water in which FDG is melted.

As with the phantoms 30, the phantoms 31 are placed in the PET effective visual field and on the side edge portion of the MRI effective visual field, as illustrated in FIGS. 9B and 9C. Furthermore, as with the phantoms 30, it is desired that the spheres of the phantoms 31 have the diameters (for example, equal to or smaller than 5 mm) within a spatial resolution of the PET. In addition, an interval at which the spheres of the phantoms 31 are scattered is desirably identical to the interval (slice interval) of image capturing by the PET and the MRI, for example.

Embodiments of the phantoms are not limited to the examples illustrated in FIGS. 6A to 6C and FIGS. 9A to 9C. For example, the length, the number, the shape, the arrangement, the direction, and the like of the phantoms can be changed optionally. For example, the cylindrical phantoms 30 have been illustrated in FIGS. 6A to 6C and the spherical phantoms 31 have been illustrated in FIGS. 9A to 9C. Alternatively, prismatic phantoms, rectangular parallelepiped phantoms, or phantoms having another shape may be employed. Furthermore, although the phantoms are arranged in the MRI effective visual field 21 at the outer side of the region 26 in FIGS. 6A to 6C and FIGS. 9A to 9C, the embodiment is not limited thereto. For example, the phantoms may be arranged in the MRI effective visual field 21 at the inner side of the region 26.

Furthermore, although all the tubes or spheres of the phantoms incorporate radioisotopes and hydrogen nuclei such that all the tubes or spheres of the phantoms are drawn on both the PET image and the MRI image in the above-mentioned embodiment and modification, the embodiment is not limited thereto. For example, when positioning of the center position on the MR image is omitted, the tube or the sphere at the center may not incorporate hydrogen nuclei (for example, water). In addition, because strain is not generated on the PET image, tubes or spheres at positions other than the center may not incorporate the radioisotopes, for example. For example, it is assumed that only the tube or the sphere at the center is expressed on the PET image and only the tubes or the spheres at positions other than the center are expressed on the MR image. In this case, for example, first, the center position of the PET image is positioned with the tube at the center that has been expressed on the PET image, and then, the positions of remaining four tubes on the PET image are obtained by calculation. Then, the strain correction factor can be derived based on the positional relation between the four tubes obtained on the PET image and the four tubes expressed on the MR image. In this manner, because the overall phantoms are not necessarily drawn on both the PET image and the MRI image, materials incorporated in the phantoms can be selected appropriately.

Other Embodiments

The embodiment is not limited to the above-mentioned embodiment and modifications thereof.

Figure 10:
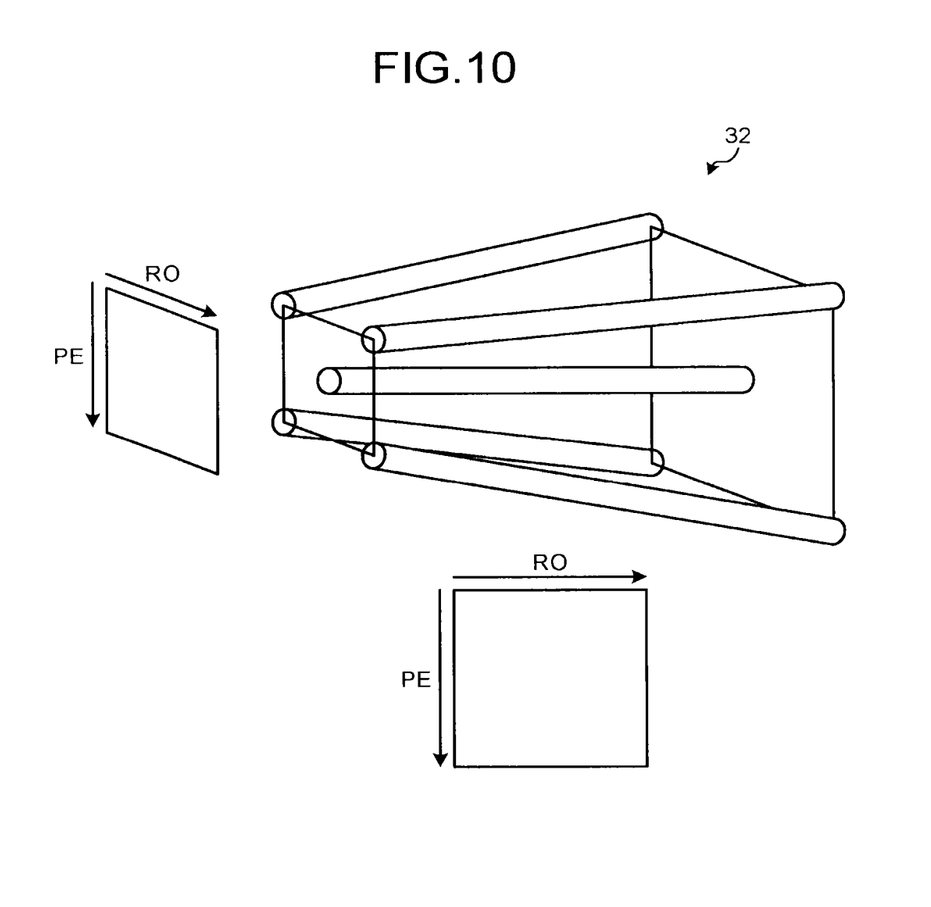
FIG. 10 is a view for explaining phantoms according to another embodiment.

FIG. 10 is a view for explaining phantoms 32 according to another embodiment. For example, when acquisition of volume data is supposed, strain on the MR image can also be generated in the shaft direction of the bore. In this case, the phantoms 32 may be arranged such that the arrangement positions of the phantoms on the slice surface change along the shaft direction. For example, as illustrated in FIG. 10, the linear phantoms 32 may include tubes on the side edge portion inclined gradually such that the distances between these tubes and the center tube are changed in accordance with the positions in the shaft direction. In this case, it is sufficient that the PET image generator 10a and the MR image generator 10b acquire the PET data and the MR data from two different directions in the read out (RO) direction, respectively, as illustrated in FIG. 10, for example. Acquiring pieces of information from the two directions can identify whether the strain of the phantoms 32 drawn on the MR image is strain generated on the slice surface or strain generated in the shaft direction of the bore. In FIG. 10, "PE" indicates the phase encode direction. In this case, scattered phantoms may be also used instead of the linear phantoms 32.

Figure 11:
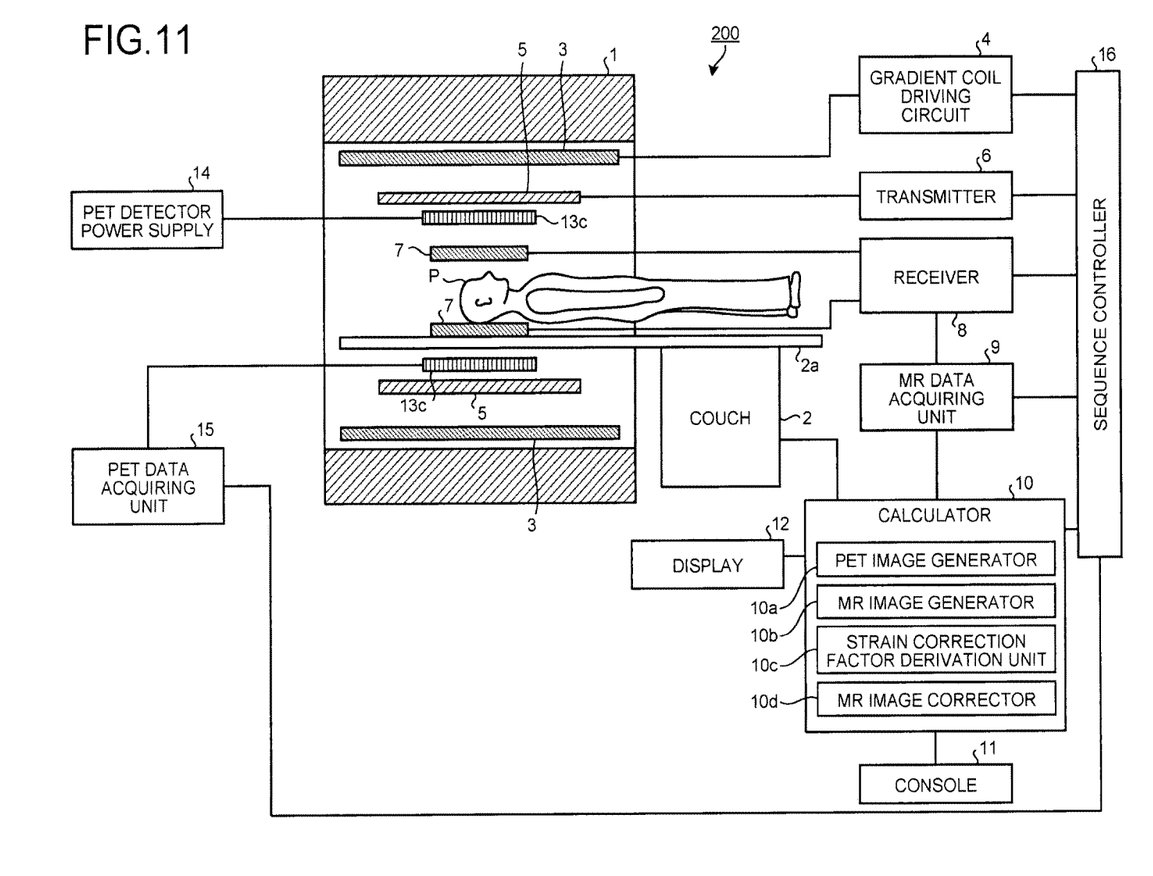
FIG. 11 is a view illustrating a configuration of a PET-MRI device according to still another embodiment.

FIG. 11 is a view illustrating a configuration of a PET-MRI device 200 according to still another embodiment. In the above-mentioned embodiments and modifications thereof, described has been the PET-MRI device 100 including two PET detectors 13a and 13b, as an example. The embodiment is not limited thereto. For example, as illustrated in FIG. 11, the PET-MRI device 200 may have a configuration including one PET detector 13c. In this case, the PET effective visual field is a region surrounded by the inner circumferential surface of the PET detector 13c.

Although it is supposed that the strain correction factor derivation processing is performed when the PET-MRI device is installed and an image of the phantoms is captured by the PET and the MRI in the above-mentioned embodiments and modifications, the embodiment is not limited thereto. For example, an image capturing target of the subject placed in the PET effective visual field may be image-captured by the PET and the MRI at the time of normal image capturing while the PET-MRI device is being operated, and the strain correction factor may be derived by using the PET image.

Although the strain correction factor is derived for each pulse sequence of the MRI in the above-mentioned embodiments and modifications, the embodiment is not limited thereto. The scintillators are elements having magnetic property in many cases, so that the PET detectors 13a and 13b using the scintillators may have an influence on the non-uniformity of the magnetostatic field. Furthermore, as described above, when the PET detectors 13a and 13b are movable along the shaft direction of the bore, the magnetic field distribution of the magnetostatic field may be different depending on the positions of the PET detectors 13a and 13b. Eventually, strain generated on the MR image due to the non-uniformity of the magnetostatic field is also different depending on the positions of the PET detectors 13a and 13b.

In consideration of this, the strain correction factor may be derived for the respective positions of the PET detectors 13a and 13b. In the procedure of the correction factor derivation processing illustrated in FIG. 5, the strain correction factor is derived while changing the pulse sequence. In the same manner, it is sufficient that the strain correction factor is derived while changing the positions of the PET detectors 13a and 13b. In this case, it is sufficient that the strain correction factor is derived for at least two arrangement states of the PET detectors 13a and 13b, and the strain correction factor is derived for other arrangement states by interpolation calculation or the like. For example, it is sufficient that the strain correction factor is derived for at least two arrangement states: the PET detectors 13a and 13b are arranged at positions at the outer-most sides in the shaft direction of the bore, that is, the distance between two detectors is the largest; and the PET detectors 13a and 13b are arranged at positions at the inner-most sides in the shaft direction of the bore, that is, the distance between the two detectors is the smallest.

Instead of the derivation by the interpolation calculation or the like, the strain correction factor may be derived finely for each arrangement state by repeating the procedure of the strain correction factor derivation processing illustrated in FIG. 5 while changing the arrangement states of the PET detectors 13a and 13b little by little. The strain correction factor may be derived for other arrangement states such as the case where the two detectors are arranged on one end in the shaft direction of the bore collectively. Alternatively, the strain correction factor may be derived for each combination of the positions of the PET detectors 13a and 13b and the pulse sequence of the MRI.

With the PET-MRI device according to at least one embodiment of the embodiments described above, strain on the MR image can be corrected appropriately.

Some embodiments of the invention have been described as examples and do not intend to limit the scope of the invention. These embodiments can be executed in a variety of other modes, and various omissions, replacements, and changes can be made without departing from the spirit and scope of the invention. These embodiments and modifications thereof are encompassed in the spirit and scope of the invention and are also encompassed in the accompanying claims and their equivalents.

What is claimed is:

1. A PET (Positron Emission Tomography)-MRI (Magnetic Resonance Imaging) device comprising:
   a magnet configured to generate a static magnetic field within a bore of the PET-MRI, which is configured to accommodate a subject to be imaged;
   a transmitting radio frequency coil configured to apply a radio frequency magnetic field on a target, which is arranged in the static magnetic field;
   a gradient coil configured to apply a gradient magnetic field on the target;
   a receiving radio frequency coil configured to detect a magnetic resonance (MR) signal emitted from the target resulting from an application of the radio frequency magnetic field and the gradient magnetic field on the target;
   a first PET detector and a second PET detector each configured to have a right shape and detect annihilation radiation emitted from a positron-emitting radionuclide in the target; and
   a processor configured to
      capture an image of the target placed in an effective visual field of a PET and on a side edge portion of an effective visual field of an MRI by the PET and the MRI so as to generate a PET image and an MR image, the PET generating the PET image based on the annihilation radiation detected by the first PET detector and the second PET detector, the MRI generating the MR image based on the MR signal detected by the receiving radio frequency coil; and
      derive a strain correction factor for correcting strain on the MR image based on a positional relation between a coordinate value of a position of the target represented on the PET image and a coordinate value of a position of the target represented on the MR image, wherein the first PET detector and the second PET detector are adjustably configured with respect to each other to adjust an interval between the first PET detector and the second PET detector, and the processor derives the strain correction factor for respective positions at which the first PET detector and the second PET detector are arranged.

2. The PET-MRI device according to claim 1, the processor is further configured to correct the MR image by using the strain correction factor.

3. The PET-MRI device according to claim 1, wherein the processor is configured to derive the strain correction factor based on the positional relation represented in the PET image and the MR image generated of the target, wherein the target is a phantom placed in the effective visual field of the PET and on the side edge portion of the effective visual field of the MRI as the target by the PET and the MRI.

4. The PET-MRI device according to claim 1, wherein the processor is further configured to derive the strain correction factor based on the PET image and the MR image generated of the target, wherein the target has an arrangement position that changes as a function of position along a shaft direction of the bore on slice surfaces of the PET image and the MRI image.

5. The PET-MRI device according to claim 1, wherein the processor is configured to derive the strain correction factor based on the positional relation represented in the PET image and the MR image generated of the target, wherein the target is a phantom incorporating a radioisotope and a hydrogen nucleus as the target by the PET and the MRI.

6. The PET-MRI device according to claim 1, wherein the processor corrects strain on the MR image based on the positional relation between the target that is expressed on the PET image with no strain due to non-uniformity of a magnetostatic field and the target that is expressed on the MR image.

7. The PET-MRI device according to claim 1, wherein the processor derives the strain correction factor for each pulse sequence of the MRI.

8. The PET-MRI device according to claim 1, wherein the processor derives the strain correction factor by deriving a coordinate conversion matrix of coordinates of the target expressed on the PET image and coordinates of the target expressed on the MRI image.

9. The PET-MRI device according to claim 1, wherein the processor is configured to derive the strain correction factor based on the positional relation represented in the PET image and the MR image generated of the target, wherein the target is a linear phantom extending in a shaft direction of the bore as the target by the PET and the MRI.

10. The PET-MRI device according to claim 9, wherein the processor is configured to derive the strain correction factor based on the positional relation represented in the PET image and the MR image generated of the target, wherein the target is the linear phantom having a thickness within a spatial resolution of the PET by the PET and the MRI.

11. The PET-MRI device according to claim 1, wherein the processor is configured to derive the strain correction factor based on the positional relation represented in the PET image and the MR image generated of the target, wherein the target is a dot-like phantom scattered in a shaft direction of the bore as the target by the PET and the MRI.

12. The PET-MRI device according to claim 11, wherein the processor is configured to derive the strain correction factor based on the positional relation represented in the PET image and the MR image generated of the target, wherein the target is the dot-like phantom having a size within a spatial resolution of the PET by the PET and the MRI.

13. The PET-MRI device according to claim 11, wherein the processor is further configured to derive the strain correction factor based on the PET image and the MR image generated of the target, wherein a spatial interval at which the dot-like phantom is scattered is identical to an interval at which images are captured by the PET and the MRI.

* * * * *